US012721886B2

(12) United States Patent
Quan et al.

(10) Patent No.: US 12,721,886 B2
(45) Date of Patent: Sep. 1, 2026

(54) VIRUS-LIKE PARTICLES CONTAINING CST1 PROTEIN AND TOXOPLASMA VACCINE USING SAME

(71) Applicant: University—Industry Cooperation Group of Kyung Hee University, Yongin-si (KR)

(72) Inventors: Fu-Shi Quan, Seoul (KR); Gi-Deok Eom, Seoul (KR); Hae-Ji Kang, Seoul (KR); Keon-Woong Yoon, Seoul (KR); Min-Ju Kim, Seoul (KR)

(73) Assignee: University-Industry Cooperation Group of Kyung Hee University, Yongin-si (KR)

( * ) Notice: Subject to any disclaimer, the term of this patent is extended or adjusted under 35 U.S.C. 154(b) by 834 days.

(21) Appl. No.: 18/054,253

(22) Filed: Nov. 10, 2022

(65) Prior Publication Data

US 2023/0149527 A1 May 18, 2023

(30) Foreign Application Priority Data

Nov. 16, 2021 (KR) ........................ 10-2021-0157349

(51) Int. Cl.

| | |
|---|---|
| ***C12N 7/00*** | (2006.01) |
| ***A61K 39/12*** | (2006.01) |
| ***A61K 39/145*** | (2006.01) |
| ***A61P 31/16*** | (2006.01) |
| ***C07K 14/005*** | (2006.01) |
| *A61K 39/00* | (2006.01) |

(52) U.S. Cl.

CPC ............ *A61K 39/12* (2013.01); *A61K 39/145* (2013.01); *A61P 31/16* (2018.01); *C07K 14/005* (2013.01); *C12N 7/00* (2013.01); *A61K 2039/5258* (2013.01); *A61K 2039/55505* (2013.01); *C12N 2760/16122* (2013.01); *C12N 2760/16123* (2013.01); *C12N 2760/16134* (2013.01)

(58) Field of Classification Search

None

See application file for complete search history.

(56) References Cited

U.S. PATENT DOCUMENTS 11,542,477 B2 * 1/2023 Park ........................ A61P 33/02

FOREIGN PATENT DOCUMENTS

| | | |
|---|---|---|
| KR | 10-2017-0118417 A | 10/2017 |
| KR | 10-2021-0099342 A | 8/2021 |
| WO | 2020-243675 A | 12/2020 |

OTHER PUBLICATIONS

Deshmukh et al (Microbial Pathogenesis, 2021, vol. 152, 104643, available online Nov. 21, 2020). (Year: 2020).*

Kumar et al. SEZL1-TOXGM (Year: 2013).*

Zhang, Y. W. et al. "Initial Characterization of CST1, a Toxoplasma gondii Cyst Wall Glycoprotein" Infection and Immunity (2001) vol. 69, No. 1, p. 501-507.

Eom, G. D. et al. "Protective effect of influenza virus like particle vaccine comprising Toxoplasma gondii cyst wall protein" Program and Abstracts of the 63rd annual meeting of the Korean Society for Parasitology and Tropical Medicine. The Korean Society for Parasitology and Tropical Medicine. The 63rd Annual Meeting and Academic Conference (2021) Oct. 28-29, 2021, with English translation.

Korean Office Action for Korean patent application No. 10-2021-0157349, dated Apr. 26, 2024, including English translation, 8 pages.

Smith, Nicholas C. et al., Review Article "Control of human toxoplasmosis", International Journal for Parasitology 51 (2021) 95-121, journal homepage: www.elsevier.com/locate/ijpara, available online Dec. 19, 2020, 27 pages.

Tomita, Tadakimi et al., "The Toxoplasma gondii Cyst Wall Protein CST1 Is Critical for Cyst Wall Integrity and Promotes Bradyzoite Persistence", Copyright: 2013 Tomita et al., published Dec. 26, 2013, PLOS Pathogens | www.plospathogens.org, Dec. 2013 | vol. 9 | Issue 12 | e1003823, 15 pages.

* cited by examiner

*Primary Examiner* — Celine X Qian

(74) *Attorney, Agent, or Firm* — Westman, Champlin & Koehler, P.A.; Amanda M. Prose

(57) ABSTRACT

Disclosed is a *Toxoplasma gondii* cyst wall protein cst1 (CST1)-containing influenza virus-like particle, which includes a core consisting of an influenza virus matrix protein 1 (M1); and the CST1 protein of *Toxoplasma gondii* displayed on a surface thereof; and a vaccine using the same.

4 Claims, 8 Drawing Sheets

Specification includes a Sequence Listing.

SEQUENCE LISTING

```
Sequence total quantity: 5
SEQ ID NO: 1            moltype = AA  length = 397
FEATURE                 Location/Qualifiers
source                  1..397
                        mol_type = protein
                        organism = synthetic construct
SEQUENCE: 1
```

-continued

```
MTAPFLRVYT DILSERKVRV EGTWHLVSIK ATHDQPLCAC KQTWSVHFAW PVDTMKLSYF  60
FFALSSSGAT LLLFAVTQLA TQVSGFDLEE PRDLRHEMKK IEVIHGSEGA RFECPVESVL  120
LPEQAMSGDI RAATVFAVAA DGSCNIFDPP SLLGDVVPGA YLQEELSVNA DKAAKTYTLV  180
IPGLPAKEVK LCYVCAHPDN PAGSQVTVIT VRRSGDSENG NPASSPVCRP SFSLEAWALG  240
VRQPSVVLDV AAPGQSVRFS CLSTATELPS EAGARPAPAQ VYPVNGRGWC DLSKGPSSLE  300
KFLLGAAMTA EVRQRGGGFL TTYTLNVPRL PSTNRRFCYV CPRNRDPADG CAVLVKVRGG  360
MVEDPIGKPA AVPTCHPQES PEGIAAGTKS AALILDI                          397

SEQ ID NO: 2            moltype = AA  length = 252
FEATURE                 Location/Qualifiers
source                  1..252
                        mol_type = protein
                        organism = synthetic construct
SEQUENCE: 2
MSLLTEVETY VLSIIPSGPL KAEIAQRLED VFAGKNTDLE VLMEWLKTRP ILSPLTKGIL  60
GFVFTLTVPS ERGLQRRRFV QNALNGNGDP NNMDKAVKLY RKLKREITFH GAKEISLSYS  120
AGALASCMGL IYNRMGAVTT EVAFGLVCAT CEQIADSQHR SHRQMVTTTN PLIRHENRMV  180
LASTTAKAME QMAGSSEQAA EAMEVASQAR QMVQAMRTIG THPSSSAGLK NDLLENLQAY  240
QKRMGVQMQR FK                                                     252

SEQ ID NO: 3            moltype = DNA  length = 1194
FEATURE                 Location/Qualifiers
source                  1..1194
                        mol_type = other DNA
                        organism = synthetic construct
SEQUENCE: 3
atgactgctc ctttttgag agtgtataca gatatacttt cggagcgtaa agtcagggta  60
gaggggacgt ggcatcttgt gtcgataaaa gcgacccacg atcagccctt gtgtgcgtgc  120
aaacaaacct ggtccgtaca tttcgcgtgg ccagtagaca caatgaaatt atcttatttc  180
tttttcgcgc tgtcaagcag tggagcaacc ctgcttttat tcgccgttac gcagctagca  240
acccaggtgt ccgggttcga tctggaagaa ccccgagatc tgaggcatga gatgaagaaa  300
atagaggtta ttcacgggag cgaaggtgcg cggttcgagt gtcctgttga gtcggtgcta  360
cttcccgagc aagcaatgtc tggcgacatt cgggctgcca cagtgtttgc tgtagccgct  420
gatggatcgt gcaacatttt cgacccgccc tccctgctcg gtgacgtagt acctggtgct  480
tacctgcagg aggagctttc ggtgaatgca gacaaggcgg caaaaacata cacgcttgtg  540
atcccaggtt tgcccgcgaa ggaggtcaaa ctctgctacg tctgcgcgca cccagataat  600
ccagcaggta gtcaggtgac ggtgatcacg gtaagacgat ctggagacag cgaaaatgga  660
aatcctgcgt catcgcccgt gtgcaggcct agtttctccc tggaggcttg ggctctaggt  720
gtgagacagc catccgtagt tctggatgtg gcggcaccag gacagtcggt gcgattttcg  780
tgtctgagca ctgccacaga gctaccaagc gaagccggag ctcgtccggc acccgcacag  840
gtatatcccg tcaatgggcg gggttggtgt gacttgtcga agggaccgtc tagcttggaa  900
aaatttcttt tgggggcggc aatgacagcg gaagttagac agcgaggtgg aggttttctg  960
acgacgtaca cgctcaatgt tcctcggctt ccgtcgacaa ataggcgatt ctgttacgtc  1020
tgcccgcgga accgtgatcc ggcggacggc tgcgcagtcc tggtgaaggt cagaggagga  1080
atggtagagg atccaatagg gaagccggcc gcagtgccga catgtcaccc ccaggagtcc  1140
ccagagggaa ttgcagcagg cacgaaaagt gctgcgttaa tactggatat ttaa       1194

SEQ ID NO: 4            moltype = DNA  length = 34
FEATURE                 Location/Qualifiers
source                  1..34
                        mol_type = other DNA
                        organism = synthetic construct
SEQUENCE: 4
atatgaattc atgactgctc ctttttgag agtg                              34

SEQ ID NO: 5            moltype = DNA  length = 34
FEATURE                 Location/Qualifiers
source                  1..34
                        mol_type = other DNA
                        organism = synthetic construct
SEQUENCE: 5
tataagcttt caaatatcca gtattaacgc agca                             34
```

VIRUS-LIKE PARTICLES CONTAINING CST1 PROTEIN AND TOXOPLASMA VACCINE USING SAME

TECHNICAL FIELD

This application claims priority to Korean Patent Application No. 10-2021-0157349, filed on Nov. 16, 2021.

The present disclosure relates to a virus-like particle including a CST1 protein and a *toxoplasma* vaccine using the same.

REFERENCE TO AN ELECTRONIC SEQUENCE LISTING

The contents of the electronic sequence listing (2022-11-10_SequenceListing.xml; Size: 7,135 bytes; and Date of Creation: Nov. 8, 2022) is herein incorporated by reference in its entirety.

BACKGROUND

*Toxoplasma gondii* is an obligate intracellular parasitic protozoan that causes toxoplasmosis. *Toxoplasma gondii* infects almost all warm-blooded animals. However, the only final host in which *Toxoplasma gondii* can sexually reproduce is felines such as domestic cats.

Cats are infected with *Toxoplasma gondii* by eating mice in which tissue cysts of toxoplasmosis have been formed. The bradyzoites released from ingested cysts infect the epithelial cells in the small intestine of cats, undergone development and reproduction inside the intestinal cells to thereby form oocysts. The infected intestinal cells rupture and release oocysts which are excreted in cat feces and then ingested by other animals to continue to spread the infection.

Tissue cysts formed by bradyzoites can be found in almost all organs, but are mainly found in the brain, eyes, and muscle tissue. The organs where tissue cysts are mainly formed vary from species to species, and most cysts are found in the brain in mice. Differentiation of bradyzoites and maintenance of cysts play an important role in *Toxoplasma gondii* infection. The parasiteophorous vacuole membrane (PVM) of tachyzoites is transformed into a cyst wall in mature bradyzoites. The cystic wall is important for evasion of the host's immune response and resistance to environmental stress, and it enables long-term survival of *Toxoplasma gondii* thus causing prolonged chronic infection. Adults infected with *Toxoplasma gondii* often do not show any obvious symptoms. However, it is known that up to 95% of the population is infected with asymptomatic toxoplasmosis. Once toxoplasmosis develops, mild flu-like symptoms that typically last for weeks to months may be shown. However, people with a weakened immune system may develop serious symptoms such as seizures, nervous system disorders, and mental disorders; in particular, if a woman becomes infected during pregnancy, it may cause miscarriage or congenital toxoplasmosis in the fetus.

Currently, there is no vaccine to prevent toxoplasmosis, and the only method known to prevent the same is to prevent the spread of zoonoses (e.g., practicing hygiene).

PRIOR DOCUMENT

Patent Document (Patent Document 0001) Korean Patent Application Publication No. 10-2017-0118417 (Oct. 25, 2017)

SUMMARY

In a specific embodiment, there is provided a CST1-containing influenza virus-like particle capable of preventing or treating *Toxoplasma gondii* infection.

An aspect of the present disclosure provides a *Toxoplasma gondii* cyst wall protein cst1 (CST1)-containing influenza virus-like particle, which includes: a core consisting of an influenza virus matrix protein 1 (M1); and an antigenic protein, wherein the antigen protein is the CST1 of *Toxoplasma gondii.*

CST1 protein is a protein that contributes to the structural integrity and persistence of cysts formed by *Toxoplasma gondii*, and deletion of CST1 may decrease the number of cysts and thickness of the cyst wall and reduce resistance to stress. The present inventors, expecting that the administration of a vaccine using CST1 as an antigen may inhibit cyst formation to thereby inhibit the *Toxoplasma gondii* infection, immunized mice by constructing a virus-like particles displaying CST1 on its surface and infected the mice with *Toxoplasma gondii*. As a result, it was confirmed that the mice inoculated with CST1 VLP, even when infected with *Toxoplasma gondii*, produced IgG and IgA antibodies specific for *Toxoplasma gondii* antigens in sera and the small intestine, produced ASC and GCB specific for *Toxoplasma gondii* antigens in the spleen, significantly reduced the expression of proinflammatory cytokines in the brain and the number of *Toxoplasma gondii* cysts, and all mice were survived, thus being effective in preventing and treating *Toxoplasma gondii* infection.

It has not been known before as to whether VLP can have an effect on preventing or treating toxoplasmosis; moreover, to which range of the residues of CST1 should be included in VLP so as to exhibit the effect on preventing or treating toxoplasmosis.

Although the virus-like particle (VLP) includes a viral protein, it is a non-infectious particle because it includes no genetic material. The virus-like particle can be synthesized by individual expression and self-assembly of the viral structural protein.

The influenza virus matrix protein 1 (M1), which is a structural protein of the influenza virus, refers to a matrix protein that forms a coat inside the envelope of the influenza virus. In an embodiment, the M1 protein can be used as a structural protein of a virus-like particle. The M1 protein may consist of the amino acid sequence of SEQ ID NO: 2.

In a specific embodiment, the CST1 may consist of the amino acid sequence of SEQ ID NO: 1. The CST1 of SEQ ID NO: 1 may be some residues including a transmembrane domain. The transmembrane domain may refer to the amino acids at positions 1 to 97 in SEQ ID NO: 1.

The CST1 protein may be one which is expressed from a vector including the nucleotide sequence of SEQ ID NO: 3 (a stop codon is linked to residues at positions 37 to 1,227 bp (i.e., a 1,191 bp) of the full-length CST1 gene).

The antigen protein may be one which is displayed on the surface of the virus-like particle or a core thereof.

The virus-like particle may be prepared by a method known to those skilled in the art, for example, may be prepared by a baculovirus expression system.

Another aspect of the present disclosure provides a vaccine composition for preventing or treating *Toxoplasma gondii* infection which includes the CST1-containing influenza virus-like particle.

The term "prevention" may refer to blocking or inhibiting progression of *Toxoplasma gondii* infection.

The term "treatment" may include improving or curing symptoms of a disease caused by *Toxoplasma gondii* infection or toxoplasmosis.

As for the CST1-containing influenza virus-like particle, the CST1 protein displayed on the surface can act as an antigen, and it is safe because it does not include any genetic material thus being freed from the risk of infection; therefore, the CST1-containing influenza virus-like particle can be used as a vaccine.

In a specific embodiment, the composition may further include an adjuvant.

The adjuvant refers to a substance or composition that is added to a vaccine or pharmaceutically active ingredients to thereby increase or affect an immune response. The adjuvant may be, for example, one selected from the group consisting of aluminum salts, toll-like receptor (TLR) agonists, monophosphoryl lipid A (MLA), synthetic lipid A, lipid A mimetics or analogs, MLA derivatives, cytokines, saponins, muramyl dipeptide (MDP) derivatives, CpG oligos, lipopolysaccharides (LPS) of Gram-negative bacteria, polyphosphazenes, emulsions, virosomes, cochleates, poly(lactide-co-glycolides)(PLGs) microparticles, poloxamer particles, microparticles, liposomes, Complete Freund's Adjuvants (CFAs), and Incomplete Freund's Adjuvants (IFAs), and as the aluminum salt, aluminum hydroxide or aluminum phosphate may be used, but is not particularly limited thereto.

The vaccine composition may be used after formulation in the form of oral formulations (e.g., powders, granules, tablets, capsules, suspensions, emulsions, syrups, aerosols, etc.) and sterile injection solutions according to conventional methods. In performing formulation, the preparations can be prepared using commonly used diluents or excipients such as fillers, extenders, binders, wetting agents, disintegrants, surfactants, etc. Solid preparations for oral administration may include tablets, pills, powders, granules, capsules, etc., and the solid preparations may be prepared by mixing at least one excipient (e.g., starch, calcium carbonate, sucrose or lactose, gelatin, etc.) with the lecithin-like emulsifier above. In addition to simple excipients, lubricants (e.g., magnesium styrate and talc) may also be used. As liquid formulations for oral administration, suspensions, solutions for internal use, emulsions, syrups, etc. may be used, and various excipients (e.g., wetting agents, sweetening agents, fragrances, preservatives, etc.) may be included in addition to water and liquid paraffin, which are commonly used simple diluents. The preparations for parenteral administration include sterile aqueous solutions, non-aqueous agents, suspensions, emulsions, and lyophilized agents. As the non-aqueous preparation and suspension, propylene glycol, polyethylene glycol, vegetable oils (e.g., olive oil), injectable esters (e.g., ethyl oleate), etc. may be used.

The administration route of the vaccine composition is not particularly limited, and may be administered for example, orally or parenterally, and specifically may be performed through oral, intravenous, intramuscular, intraarterial, intramedullary, intrathecal, intracardiac, transdermal, subcutaneous, intraperitoneal, intranasal, intestinal, topical, sublingual, or rectal administration. Parenteral administration may include subcutaneous, intradermal, intravenous, intramuscular, intraarticular, intrasynovial, intrasternal, intrathecal, intralesional and intracranial injections.

The administration dose of the vaccine composition may be selected in consideration of the individual's age, weight, sex, physical conditions, etc. The amount required to induce an immune response in an individual without any side effects may vary depending on the presence of VLPs and other components used as immunogens, and this may be determined by methods known to those skilled in the art.

Still another aspect provides a method for preparing a CST1-containing influenza virus-like particle, which includes: co-infecting an insect cell with i) a recombinant baculovirus expressing influenza virus matrix protein 1 (M1) and ii) a recombinant baculovirus expressing the CST1 of *Toxoplasma gondii*; and culturing the co-infected insect cell and purifying virus-like particles.

The co-infection may be one in which the recombinant baculovirus expressing the CST1 of *Toxoplasma gondii* and the recombinant baculovirus expressing influenza virus matrix protein 1 (M1) (CST-rBV:M1-rBV) at a 3:1 ratio.

Still another aspect provides a composition for preparing a CST1-containing influenza virus-like particle, which includes: a recombinant baculovirus expressing influenza virus matrix protein 1 (M1); and a recombinant baculovirus expressing the CST1 of *Toxoplasma gondii*.

Advantageous Effects

In an embodiment, the CST1 VLP may be used as a vaccine composition for preventing or treating *Toxoplasma gondii* infection.

Figure 2A:
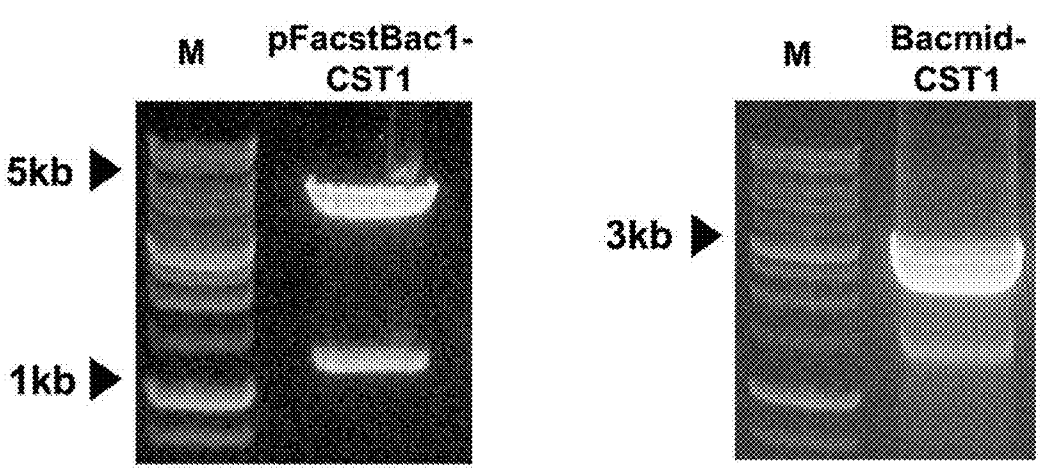

The left side of FIG. 2A shows the result of confirming the insertion of CST1 gene (pFacstBac1-CST1) by electrophoresis of the pFastBac1 vector, into which the CST1 gene was inserted, after treatment with restriction enzymes; and the right side of FIG. 2A shows the result of confirming the insertion of CST1 gene (Bacmid-CST1) by electrophoresis of bacmid obtained from the colonies of transformed DH10bac *E. coli* after PCR.

Figure 2B:

FIG. 2B shows the result of Western blot of the CST1 VLP prepared according to an embodiment after reacting with an antibody obtained from the serum of a mouse infected with *Toxoplasma gondii* and influenza M1 single antibody.

Figure 2C:
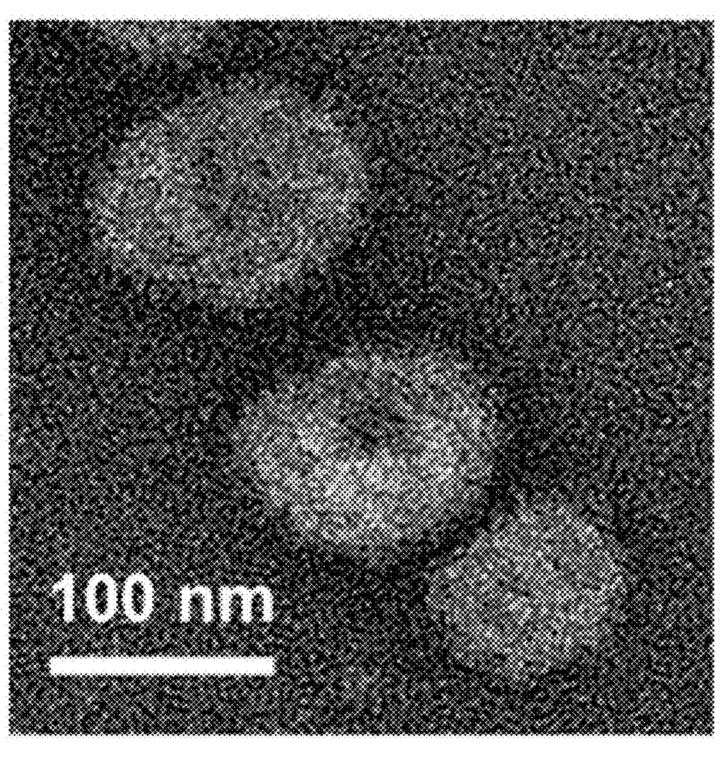

FIG. 2C shows the result of confirming by TEM the VLP, which includes M1 protein as a core protein and in which CST1 is displayed on the surface.

Figure 3A:
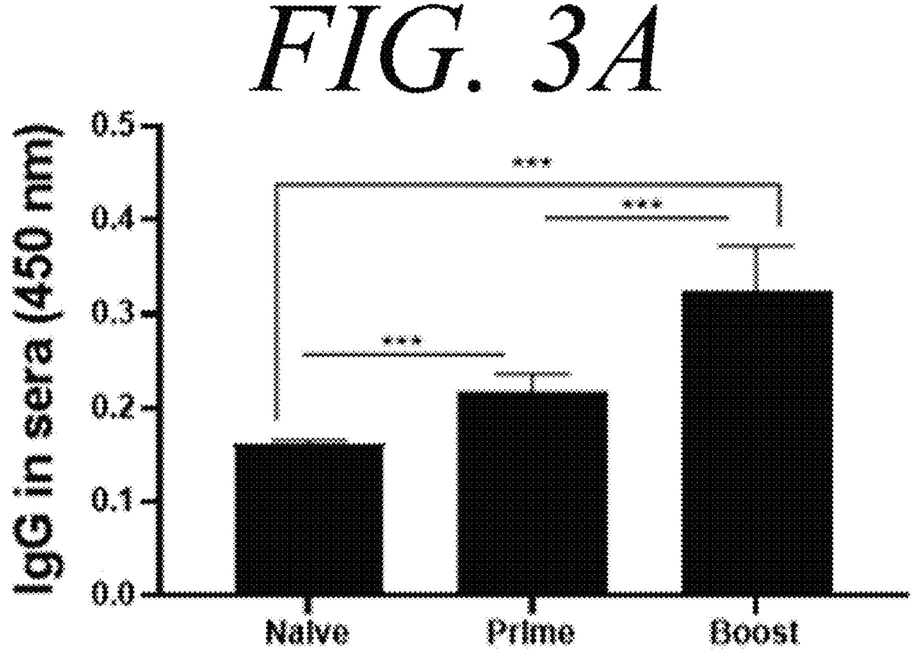

FIG. 3A shows the results of analyzing the *Toxoplasma gondii*-specific IgG antibody titer in the serum collected from an unvaccinated group (Naive), a group primary vaccinated with CST1 VLP vaccine (Prime), a group secondary vaccinated with CST1 VLP vaccine (Boost).

Figure 3B:
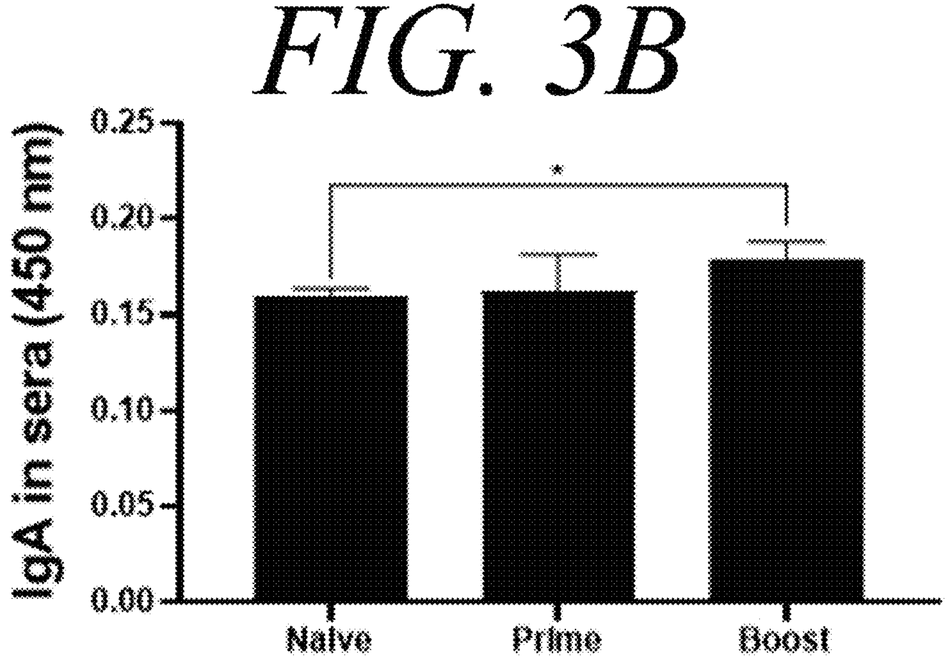

FIG. 3B shows the results of analyzing the *Toxoplasma gondii*-specific IgA antibody titer in the serum collected from an unvaccinated group (Naive), a group primary vaccinated with CST1 VLP vaccine (Prime), a group secondary vaccinated with CST1 VLP vaccine (Boost).

Figure 4A:
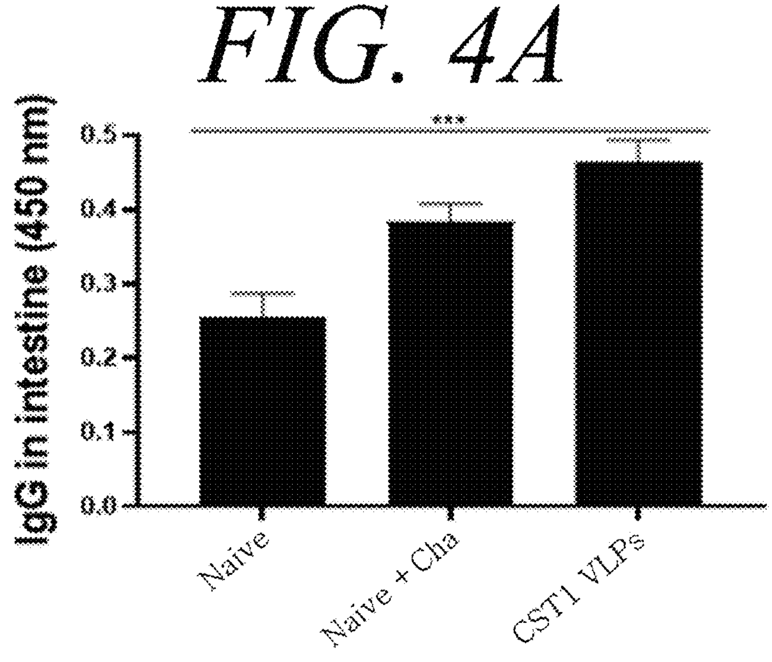

FIG. 4A shows the results of confirming the *Toxoplasma gondii*-specific IgG antibody titer in the small intestine of an unvaccinated and uninfected group (Naive), a CST1 VLP vaccinated and infected group (CST1 VLPs), and an unvaccinated and infected group (Naive+Cha).

Figure 4B:
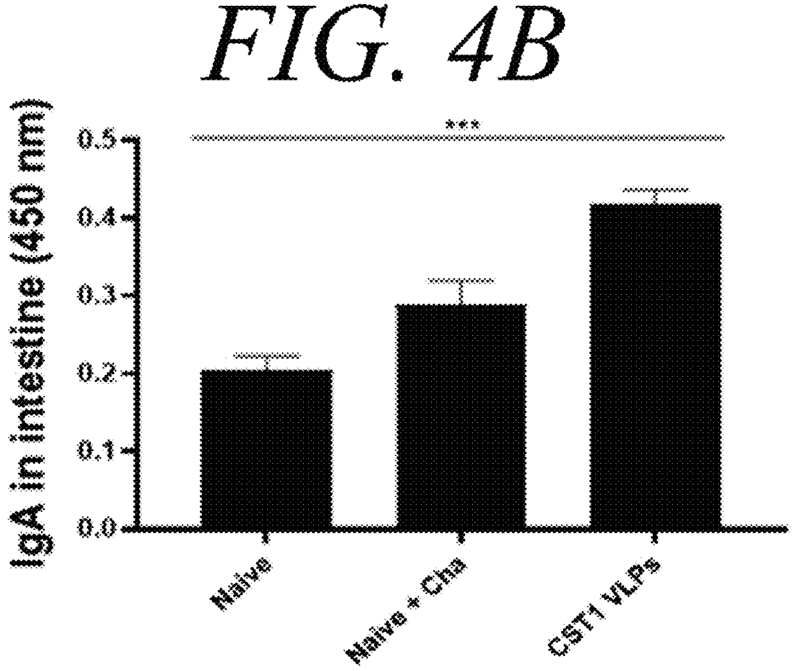

FIG. 4B shows the results of confirming the *Toxoplasma gondii*-specific IgA antibody titer in the small intestine of an unvaccinated and uninfected group (Naive), a CST1 VLP vaccinated and infected group (CST1 VLPs), and an unvaccinated and infected group (Naive+Cha).

Figure 5:
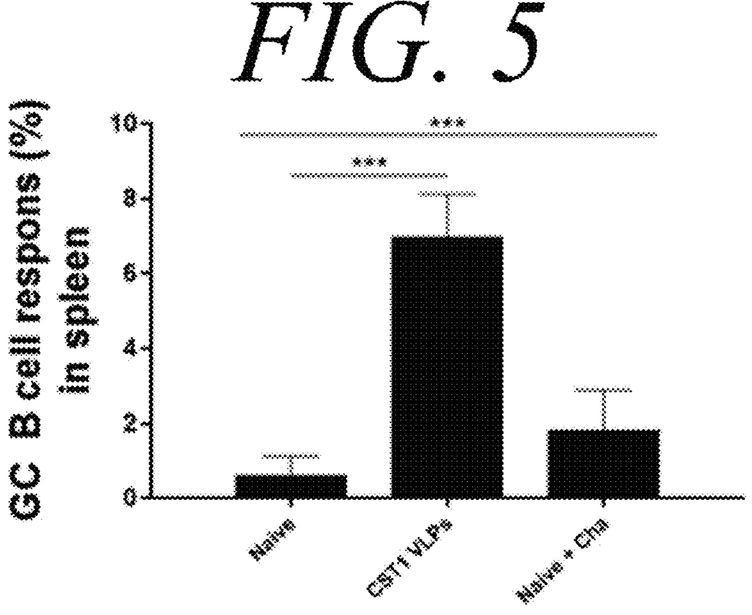

FIG. 5 shows the results of confirming the germinal center (GC) B cell population in the spleen obtained from an unvaccinated and uninfected group (Naive), a CST1 VLP vaccinated and infected group (CST1 VLPs), and an unvaccinated and infected group (Naive+Cha).

Figure 6:
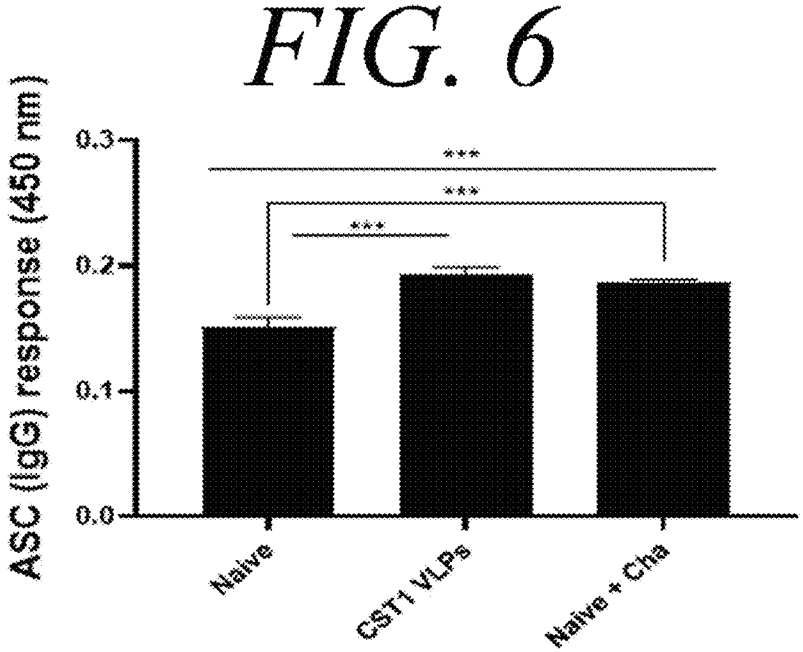

FIG. 6 shows the results of confirming the *Toxoplasma gondii*-specific IgG antibody produced in splenocytes obtained from an unvaccinated and uninfected group (Naive), a CST1 VLP vaccinated and infected group (CST1 VLPs), and an unvaccinated and infected group (Naive+Cha) after stimulating the splenocytes with *Toxoplasma gondii* antigens.

Figure 7A:
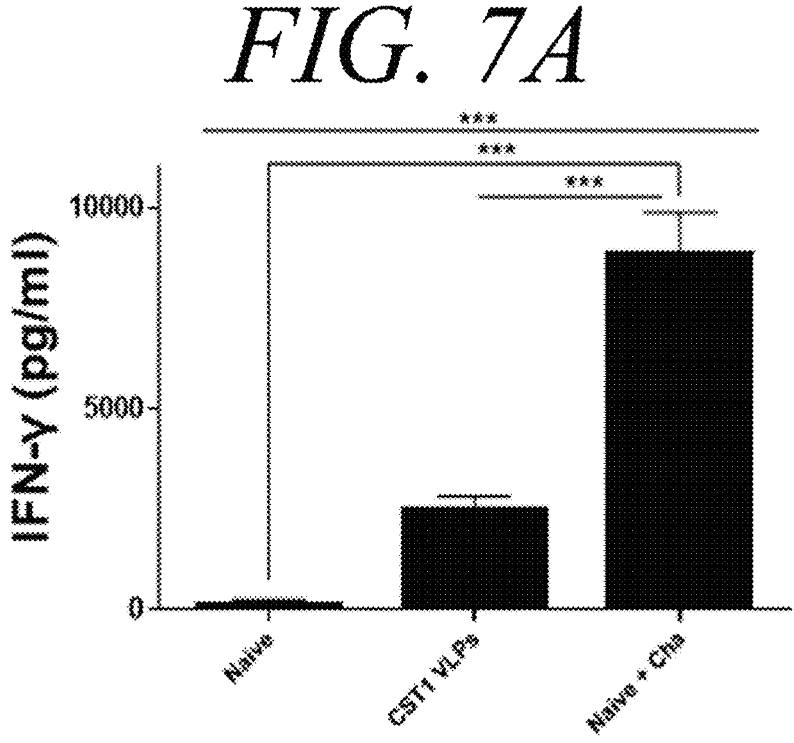

FIG. 7A shows the results of measuring the expression level of the proinflammatory cytokine IFN-7 after collecting the brains from an unvaccinated and uninfected group (Naive), a CST1 VLP vaccinated and infected group (CST1 VLPs), and an unvaccinated and infected group (Naive+Cha).

Figure 7B:
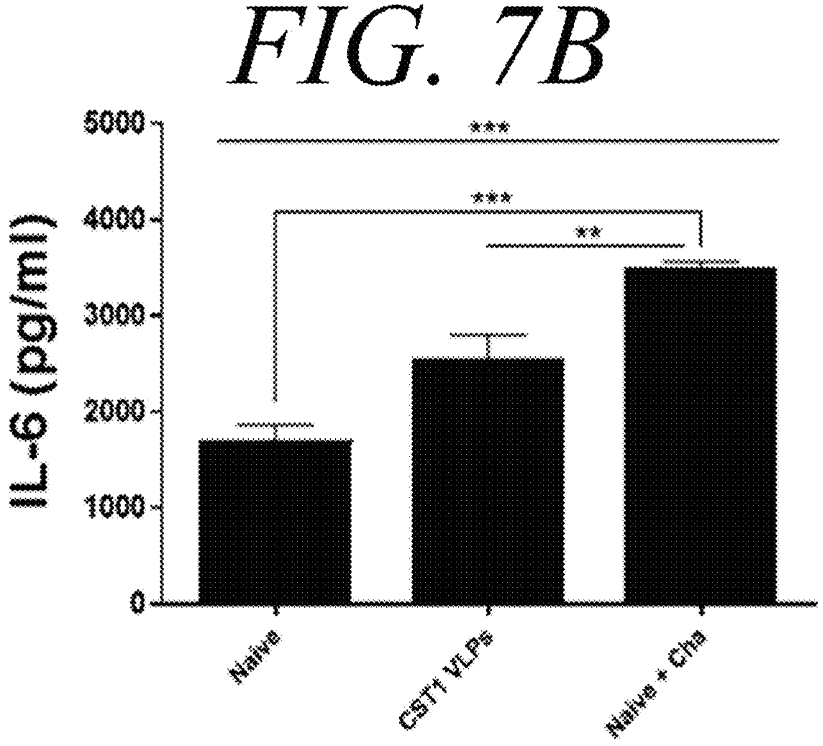

FIG. 7B shows the results of measuring the expression level of the proinflammatory cytokine IL-6 after collecting the brains from an unvaccinated and uninfected group (Naive), a CST1 VLP vaccinated and infected group (CST1 VLPs), and an unvaccinated and infected group (Naive+Cha).

Figure 8A:
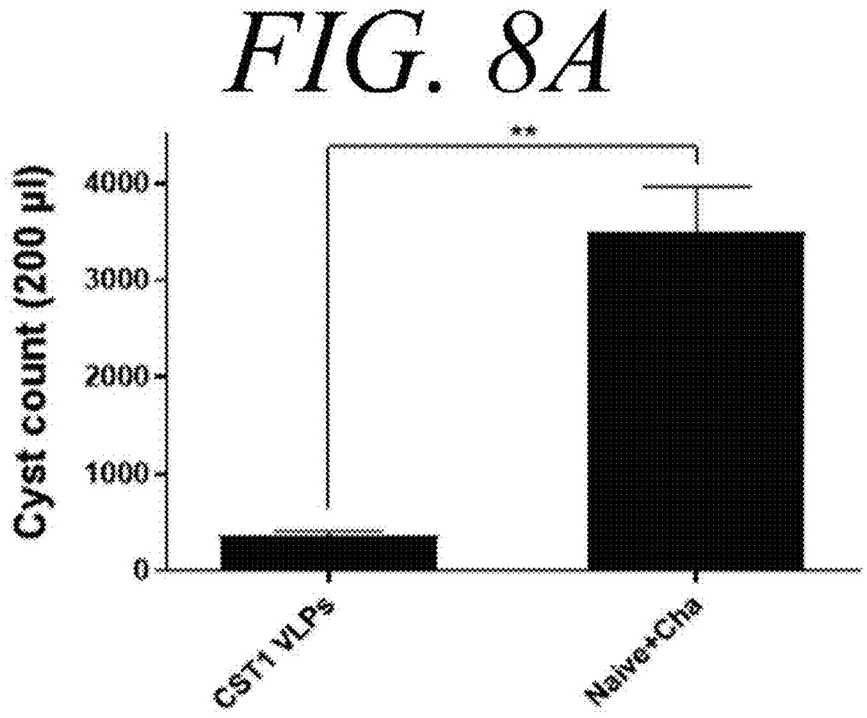

FIG. 8A shows the results of confirming the number of *Toxoplasma gondii* ME49 cysts in the brain of a CST1 VLP vaccinated and infected group (CST1 VLPs) and an unvaccinated and infected group (Naive+Cha).

Figure 8B:
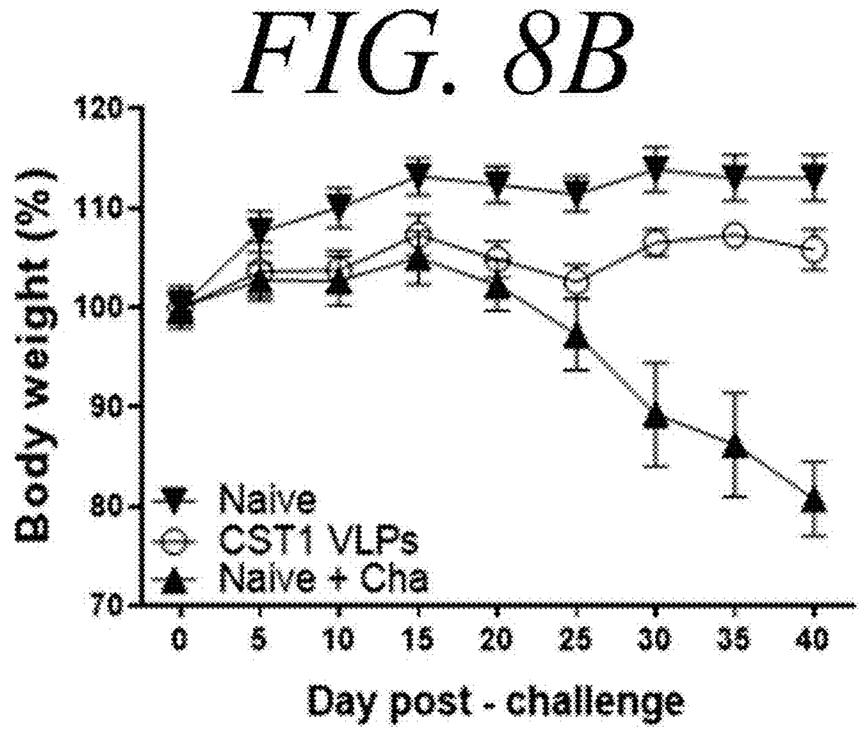

FIG. 8B shows the results of confirming the body weight over time of an unvaccinated and uninfected group (Naive), a CST1 VLP vaccinated and infected group (CST1 VLPs), and an unvaccinated and infected group (Naive+Cha).

Figure 8C:
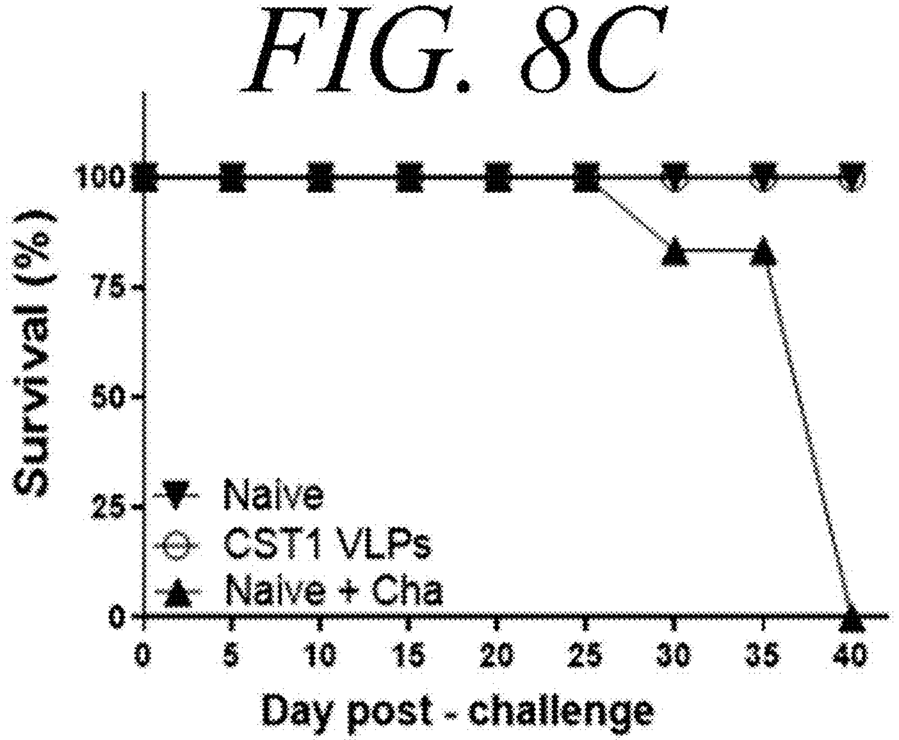

FIG. 8C shows the results of confirming the survival period of an unvaccinated and uninfected group (Naive), a CST1 VLP vaccinated and infected group (CST1 VLPs), and an unvaccinated and infected group (Naive+Cha).

DETAILED DESCRIPTION

Hereinafter, one or more specific embodiments will be described in more detail through Examples. However, these Examples are for illustrative purposes of one or more embodiments, and the scope of the present invention is not limited to these Examples.

Experimental Method

1. Compliance of Ethics on Animal Experiments

All animals were used in accordance with IACUC guidelines and the experimental protocol approved by the Animal Experimental Ethics Committee of Kyung Hee University. Euthanasia was performed in a $CO_2$ chamber.

2. Preparation of Mice, Cells, Parasites, and Antibodies

Seven-week-old BALB/c female mice were purchased from NARA Biotech (Seoul, Korea). *Spodoptera frugiperda* (Sf9) cells were cultured in SF900II medium (Invitrogen) at 27° C. and 140 rpm and used for the production of rBV and VLP. *T. gondii* ME49 was collected by infection with BALB/c mice, and sera from infected mice were collected and used as antibodies. Horseradish peroxidase (HRP)-conjugated goat anti-mouse IgG and IgA used were purchased from Southern Biotech (Birmingham, USA). 7

3. Prediction of Transmembrane of CST1 and its Cloning

The transmembrane structure was analyzed by performing in silico analysis of the amino acid sequence of the CST1 protein with Phobius (Stockholm Bioinformatics Center). Full-length CST1 RNA was extracted from *T. gondii* ME49 cysts using the RNeasy Mini Kit (Qiagen, Valencia, CA, USA).

A part of the CST1 gene (see GenBank Accession No. XM_002368554.2) was PCR-primer (forward primer: 5'-amplified using a ATATGAATTCATGACTGCTCCTTTTTTGAGAGTG-3' (SEQ ID NO: 4); reverse primer: 5'-TATAAGCTTTCAAATATCCAGTATTAACGCAGCA-3' (SEQ ID NO: 5)), and the amplified product was cloned into pFastbac 1 (Invitrogen) containing restriction enzyme sites (EcoRI, HindIII sites).

The CST1 gene residue inserted into the vector was subjected to restriction enzyme treatment and DNA sequencing, and it was confirmed that the residue consists of the sequence of SEQ ID NO: 3 (the 37th to the 1,227th (1,191 bp) and the stop codon of the CST1 gene). DH10Bac competent cells were transformed with recombinant pFastbac1 into which the CST1 gene was inserted. Colonies were cultured in LB medium containing 50 μg/mL kanamycin, 10 μg/mL tetracycline, and 7 μg/mL gentamycin, and white colonies were subjected to PCR using M13 Primer set (Sigma-Aldrich), and the transposition of the CST1 gene was confirmed through electrophoresis. The recombinant bacmid was extracted from DH10bac cells in which the transposition was confirmed using the Plasmid SV kit (GeneALL) and stored at −20° C. The influenza M1 protein gene was cloned by the previously described method. (see Virus-like particle vaccine induces protective immunity against homologous and heterologous strains of influenza virus)

4. Recombinant Baculovirus (rBV) and Generation of Virus-Like Particles (VLP) Generation Sf9 cells were transfected with the previously prepared recombinant bacmid and Cellfectin II reagent (Invitrogen) according to the manufacturer's manual.

To generate VLPs containing both CST1 and M1, Sf9 cells were co-infected with CST1-expressing rBV and M1-expressing rBV. Sf9 cells at a concentration of $2.5\times10^6$ cells/mL were co-infected with CST1-expressing recombinant baculovirus and M1-expressing recombinant baculovirus at a 3:1 ratio and cultured at 27° C. and 140 rpm for 3 days.

The infected Sf9 cell culture was centrifuged at 4° C. at 6,000 rpm for 30 minutes to remove cells and debris. VLPs were pelleted by high-speed centrifugation of the supernatant containing VLPs at 4° C. at 45,000×g for 30 minutes.

The pelleted VLPs were resuspended in PBS to purify the VLPs by a 20-30-60% sucrose cushion gradient method and washed with PBS. The concentrations of VLPs were measured using the QuantiPro BCA Assay Kit (Sigma-Aldrich, St Louis, USA) and then stored at 4° C.

5. Characterization of VLPs

VLPs were characterized by transmission electron microscopy (TEM) and Western blot.

The VLP surface was negatively stained with 1.5% phosphotungstic acid (pH 7.0) before TEM imaging.

VLPs were separated by SDS-PAGE and transferred to a nitrocellulose membrane. The membrane was blocked with 5% skim milk at room temperature for 30 minutes and washed 3 times with TBST at room temperature for 10 minutes. The CST1 protein was treated on a membrane after a 1:500 dilution of the primary antibody obtained from BALB/c mice 4 weeks after the infection with *T. gondii* ME49 strain, and incubated at 4° C. overnight.

The M1 protein was confirmed using a monoclonal mouse anti-M1 antibody. On the next day, the membrane was washed 3 times with TBST at room temperature for 10 minutes, treated with HRP-conjugated secondary antibody (a 1:2000 dilution) and incubated at room temperature for 1 hour. After washing the membrane with TBST, proteins were confirmed by enhanced chemiluminescence (ECL) with ChemiDoc Imagers (BIO-RAD, California, USA).

6. Immunization and Challenge Infection

For immunization, a total of 18 BALB/c mice were divided into three groups. Each group contained six animals, in which Group 1 was used as a control group, and Groups 2 and 3 were used as experimental groups. Group 1 is a naive group that is not vaccinated and has never been in contact with an infectious agent; Group 2 is an experimental group that is not vaccinated and infected; and Group 3 is an experimental group that is not vaccinated with VLP and infected. The mice in Group 3 were first inoculated with 50 μL of PBS containing 50 μg of VLPs through the nasal route (an intranasal route, i.n.), and then boost-vaccinated with 50 μg of VLPs four weeks after the inoculation. Four weeks after the boost inoculation, 450 cysts obtained from the brains of *Toxoplasma gondii*-infected mice were orally administered to the mice.

The cysts of *Toxoplasma gondii* used for challenge infection were obtained by the following method. *Toxoplasma gondii*-infected mice were euthanized and their brain tissues were collected and homogenized. Brain tissue homogenates were carefully stacked on percoll in a tube at a 1:2 (percoll: homogenate) ratio and centrifuged at 4° C. and 12,100 rpm. The supernatant was removed, and the collected cysts were resuspended in 200 μL of PBS and used for challenge infection.

7. *T. gondii* ME49-Specific Antibody IgG and IgA Responses

Sera were collected from mice three weeks after immunization by retro-orbital plexus puncture. The sera were centrifuged at 4° C. at 3,000 rpm for 10 minutes. 35 days after the infection (35 dpi, days per infection), the infected mice were sacrificed and their intestines were obtained. The duodenums of the mice were sliced vertically and immersed in 500 μL of PBS. Samples were incubated at 37° C. for 1 hour and centrifuged at 5,000 rpm for 10 minutes to obtain supernatants.

A *T. gondii* ME49-specific antibody response was confirmed in sera and intestines by the ELISA method. Specifically, a flat-bottom 96-well microtitration plate (SPL Life Sciences, Pocheon, Korea) was coated at 4° C. overnight with 4 μg/well of *T. gondii* ME49 antigens in 0.05 M (pH 9.6) bicarbonate buffer.

The coated plate was washed three times with PBS containing 0.05% Tween-20 (PBST) and then incubated with 0.2% gelatin (PBST solvent) at room temperature for 30 minutes to block non-specific binding. After washing with PBST, the plate was incubated with a 1:50 dilution of mouse serum in PBS at 37° C. for 1 hour. The plate was then washed and incubated at 37° C. for 1 hour with horseradish peroxidase (HRP)-conjugated goat anti-mouse IgG and IgA diluted in PBS at a 1:2000 ratio. Ophyenyldiamine (OPD) (Sigma Aldrich, St Louis, USA) was added to develop a color reaction. The colorimetric change was stopped with 2 N $H_2SO_4$ and measured at 450 nm with a microplate reader (EZ Read 400, Biochrom Ltd.).

8. Antibody-Secreting Cell Response

Spleens were collected from mice sacrificed 35 days after infection. Single cell suspensions of splenocytes were prepared as previously described (Influenza Virus-Like Particles Presenting Both *Toxoplasma gondii* ROP4 and ROP13 Enhance Protection Against *T. gondii* Infection) and the cells were counted under a microscope using a hemocytometer.

A 96-well cell culture plate was coated at 4° C. overnight with 5 g/mL of *T. gondii* ME49 antigen in 0.05 M carbonate bicarbonate buffer (pH 9.6). After washing 3 times with PBST, the plate was blocked with 0.2% gelatin at room temperature for 30 minutes. Splenocytes were spread on a plate as many as $1\times10^6$ cells and cultured in RPMI-1640 medium supplemented with 10% FBS and 1% penicillin/streptomycin in a $CO_2$ incubator at 37° C. for 5 days. After incubation, the supernatant was removed and treated with HRP-conjugated goat anti-mouse IgG diluted 1:2000 in PBS and incubated at 37° C. for 1 hour. OPD was used for color development after washing. The colorimetric change was stopped by 2 N $H_2SO_4$ and measured at 450 nm with a microplate reader.

9. Germinal Center B (GC B) Response Analysis by Flow Cytometry

Splenocytes were isolated from the mice 5 days after infection, and flow cytometry was performed. As many splenocytes as $1\times10^6$ cells were stimulated with *T. gondii* ME49 antigen (4 μg/mL) in RPMI-1640 medium containing 10% FBS and 1% penicillin/streptomycin, and cultured at 37° C. for 2 hours. After antigen stimulation, cells were stained with fluorescent binding antibodies GL7 (PE) (BD Biosciences) and B220 (FITC) (Invitrogen). All flow cytometry procedures were performed according to the manufacturer's protocol. Stained samples were analyzed using an Accuri C6 flow cytometer and C6 Accuri software (BD Biosciences, Franklin Lakes, NJ, USA).

10. Pro-Inflammatory Cytokine Assay

Brain tissue was collected from mice sacrificed 35 days after infection. Mouse brain tissue was homogenized in 500 μL of PBS and centrifuged. The supernatant and the pellet were stored separately without discarding. The pellet was used for parasite load measurement (count of cysts) and the supernatant was used for cytokine analysis. Levels of the proinflammatory cytokines IFN-7 and IL-6 were measured with the BD OptEIA ELISA kit (BD Biosciences, Franklin Lakes, NJ, USA) according to the manufacturer's protocol. The results were expressed as picograms/mL based on the standard curve generated.

11. Parasite Burden—Count of Cysts in Brain

Brain cysts collected from mice sacrificed 35 days after infection were isolated. The number of cysts contained in 5 μL of the cyst suspension was counted on a slide glass and through a microscope.

12. Statistical Analysis

All statistical analyses were expressed as mean±SD. The results were analyzed by Student t test and one-way ANOVA test followed by Dunnets or Tukey post-hoc tests in a manner appropriate for each case using GraphPad Prism version 8 software. P values (*<0.05, <0.01, *<0.001) were considered statistically significant.

Example 1: Analysis of Transmembrane Structure of CST1

The transmembrane structure was analyzed by performing in silico analysis of the amino acid sequence of CST1 protein with Phobius (Stockholm Bioinformatics Center).

Figure 1:
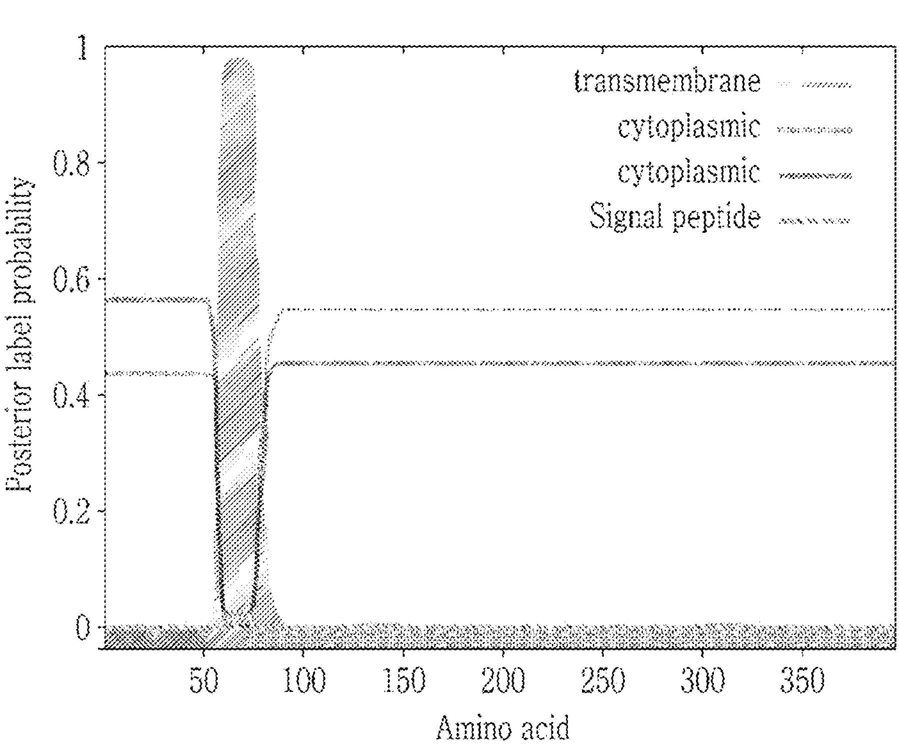
FIG. 1 shows the result of analyzing the transmembrane structure by performing in silico analysis of the amino acid sequence of CST1 protein with Phobius (Stockholm Bioinformatics Center).

In FIG. 1, the x-axis represents the position of an amino acid and the y-axis represents the probability that the amino acid at the corresponding position occupies each region or domain. According to the prediction of the transmembrane domain, it was predicted that the CST1 protein would be able to bind to the M1 core protein because it has a transmembrane domain.

Example 2: Preparation of Virus-Like Particles (VLP) Containing CST1 and M1

According to the above experimental method, a part of the CST1 gene (GenBank: Accession No. XM_002368554.2) was amplified and introduced into the pFastbac 1 plasmid to prepare a recombinant vector. DH10Bac competent cells were transformed with the recombinant vector, and thereby Bacmid into which the CST1 gene was introduced was obtained.

According to the left side of FIG. 2A, as a result of the restriction enzyme treatment and electrophoresis of the pFastBac1 vector, into which the CST1 gene was inserted, the CST1 gene (about 1.2 kb) was detected, thus confirming the successful insertion of CST1.

According to the right side of FIG. 2A, as a result of colony PCR amplification and electrophoresis of the bacmid obtained from the transformed DH10bac *E. coli* colony, a band of about 3.5 kb appeared, in which the band size was 2.3 kb when pFastbac1 was inserted and the band size was 3.5 kb when pRastbac1 including CST1 was inserted, thus confirming the successful insertion of the CST1 gene into bacmid.

The bacmid was transfected into Sf9 cells to obtain CST1-expressing rBV. The Sf9 cells were co-infected with the CST1-expressing rBV and the M1-expressing rBV to express and purify VLPs containing CST1 and M1.

FIG. 2B shows the results of Western blot after reacting the prepared CST1 VLPs with CST1 antibody obtained from the sear of *Toxoplasma gondii*-infected mice and influenza M1 single antibody. As a result, both the 43 kDa CST1 protein and the 28 kDa M1 protein were identified, thus confirming the successful preparation of the CST1 VLP.

In addition, according to the TEM photograph of FIG. 2C, it was confirmed that VLPs, in which the M1 protein formed a core and CST1 was displayed on the surface thereof, were successfully prepared.

Example 3: Confirmation of IgG- and IgA-Specific Antibody Responses in Immunized Animal Models According to the experimental method above, IgG- and IgA-specific antibody responses were confirmed in the sera collected from mice vaccinated with the CST1 VLP of *Toxoplasma gondii*. The mice prime-boosted with CST1 VLP were infected with *Toxoplasma gondii* (ME49 strain) at a lethal dose. After obtaining the intestines and brains of the infected mice, the IgG- and IgA-specific antibody responses were examined. In addition, the immune cell responses and antibody-secreting cell responses were examined in the spleen of the infected mice.

According to FIG. 3, it was found that the IgG and IgA antibody titers of the CST1 VLP vaccine-inoculated group were significantly increased compared to those of the group of non-immunized mice. In particular, high levels of IgG and IgA antibody responses were observed in the sera collected from the mice with secondary-vaccination (boost vaccination).

After infecting the CST1 VLP vaccine-inoculated mice with a lethal dose of *Toxoplasma gondii*, the intestines and brains were collected, and the *Toxoplasma gondii*-specific IgG and IgA antibody titers were examined by ELISA analysis.

According to FIG. 4, the IgG, IgA antibody titers in the small intestine of the VLP-vaccinated group were significantly increased compared to the non-immunized control group (Naive) and the parasite-infected control group (Naive+Challenge (Cha)). Through the above, it was confirmed that a mucosal immune response was exhibited in the small intestine.

After infecting the CST1 VLP vaccine-inoculated mice with a lethal dose of *Toxoplasma gondii*, their spleens were collected to examine the population of the germinal center B cells. In addition, the collected splenocytes were cultured for 5 days and the supernatant was collected, and the IgG antibody response was examined by ELISA analysis.

According to FIG. 5, the spleen of the CST1 VLP vaccine-inoculated mice showed a significant increase of germinal center B cells compared to the non-immunized control group.

According to FIG. 6, the splenocytes of the CST1 VLP vaccine-inoculated mice showed a significant increase of the IgG antibody titer response compared to the non-immunized control group (the antibody secreting cell (ASC) response in the spleen was shown to be high).

Example 4: *Toxoplasma Gondii* Protective Efficacy of CST1 VLP Vaccine

The CST1 VLP vaccine-inoculated mice were infected with a lethal dose of *Toxoplasma gondii* (ME49 strain). After 35 days of the infection, their brain tissues were collected and the reduction of pro-inflammatory cytokines and cysts in the brain were confirmed.

According to FIG. 7, the expression levels of the proinflammatory cytokines IFN-7 and IL-6 were significantly lower in the mice immunized with the CST1 VLP vaccine compared to the non-immunized control group. From the result, it was found that the CST1 VLP vaccine-inoculated group had less inflammatory responses even when infected with *Toxoplasma gondii.*

According to FIG. 8, the mice immunized with the CST1 VLP vaccine showed a significant decrease in the number of cysts in the brain compared to the non-immunized infected control group (see FIG. 8A). In addition, as a result of examining the body weight and survival period of the infected mice, the body weight decreased in all experimental groups (infected groups) until the 25th day after infection, in which while all of the mice in the Naive+Cha experimental group died on the 40th day after infection, the CST1 VLP vaccine-inoculated group showed a recovery of body weight and a 100% survival rate after 25 days (see FIGS. 8B and 8C).

What is claimed is:

1. A *Toxoplasma gondii* cyst wall protein cst1 (CST1)-containing influenza virus-like particle, comprising:
   a core consisting of a influenza virus matrix protein 1 (M1); and
   an antigenic protein,
   wherein the antigen protein is the CST1 of *Toxoplasma gondii*, and
   the CST1 consists of the amino acid sequence of SEQ ID NO: 1.

2. A vaccine composition for preventing or treating *Toxoplasma gondii* infection comprising the CST1-containing influenza virus-like particle of claim 1.

3. The vaccine composition of claim 2, further comprising an adjuvant.

4. A method for preparing a CST1-containing influenza virus-like particle, comprising:
   co-infecting an insect cell with i) a recombinant baculovirus expressing influenza virus matrix protein 1 (M1) and ii) a recombinant baculovirus expressing the CST1 of *Toxoplasma gondii*; and
   culturing the co-infected insect cell and purifying virus-like particles,
   wherein the CST1 consists of the amino acid sequence of SEQ ID NO: 1.

* * * * *